(12) United States Patent
Igushi et al.

(10) Patent No.: US 6,236,458 B1
(45) Date of Patent: May 22, 2001

(54) PARTICLE SIZE DISTRIBUTION MEASURING APPARATUS, INCLUDING AN ARRAY DETECTOR AND METHOD OF MANUFACTURING THE ARRAY DETECTOR

(75) Inventors: Tatsuo Igushi; Yoshiaki Togawa, both of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/443,985

(22) Filed: Nov. 19, 1999

(30) Foreign Application Priority Data

Nov. 20, 1998 (JP) .................................................. 10-331106

(51) Int. Cl.$^7$ .................................................... G01N 15/02
(52) U.S. Cl. ........................................... 356/336; 250/574
(58) Field of Search .................................. 356/335, 336, 356/337, 338, 340, 341, 342, 343; 250/574, 575

(56) References Cited

U.S. PATENT DOCUMENTS

| 4,274,741 | * | 6/1981 | Cornillault | 356/336 |
| 4,882,478 | * | 11/1989 | Hayashi et al. | 356/343 |
| 4,953,978 | * | 9/1990 | Bott et al. | 356/336 |
| 5,619,324 | * | 4/1997 | Harvill et al. | 356/336 |
| 5,936,729 | * | 8/1999 | Igushi | 356/336 |
| 6,061,131 | * | 5/2000 | Igushi et al. | 356/336 |

\* cited by examiner

*Primary Examiner*—Frank G. Font
*Assistant Examiner*—Sang H. Nguyen
(74) *Attorney, Agent, or Firm*—Price and Gess

(57) ABSTRACT

A particle distribution size measuring apparatus incorporates a detector array having a plurality of light detecting elements located on a substrate. A first group of detector elements have a plurality of sectors with a common sector angle, while at least one other detector element is positioned furthest from an optical axis and has a smaller sector angle. Each of the detector elements can be formed on a single substrate and their position and alignment have increased the efficiency of manufacturing the arrays.

5 Claims, 5 Drawing Sheets

PARTICLE SIZE DISTRIBUTION MEASURING APPARATUS, INCLUDING AN ARRAY DETECTOR AND METHOD OF MANUFACTURING THE ARRAY DETECTOR

BACKGROUND OF THE INVENTION

1. Field of the Invention

The present invention relates to a particle size distribution measuring apparatus, and more particularly to an array detector used in the measuring apparatus of a configuration to maximize production yield and a manufacturing method for forming a plurality of array detectors.

2. Description of Related Art

A particle size distribution measuring apparatus has been provided with a limited array detector having a plurality of light detecting elements (devices) for detecting an intensity of scattering light at various scattering angles when a laser beam from a laser beam source is irradiated onto dispersed particles.

FIG. 4 schematically shows the principal parts of a conventional particle size distribution measuring apparatus. A circulating type cell 1 (flow cell) comprising a transparent container, receive a sample solution 2 prepared by dispersing a particle group of a sample target for measurement in a proper dispersion medium. A laser beam source section 3 is located on one side (rear side) of the cell 1. The laser beam source section 3 is composed of a laser beam source 5 comprising a He-Ne laser emitting a parallel laser beam 4, towards mirrors 6 and 7 for changing a traveling direction of the laser beam 4 by an angle of 90°, and a beam expander 8 for properly enlarging the parallel laser beam 4 in a light (beam) flux direction.

A collective (condenser) lens 9 is located on the other side (front side) of the cell 1, and a ring-like array detector 10 is arranged on a focal position. As shown in FIG. 5, the array detector 10 comprises a transmitted light detecting element 11 which is formed on a position corresponding to an optical axis of the collective lens 9, and a scattering light detecting element group 12 for detecting scattered light 4A. The scattering light detecting group 12 comprises a plurality of circular-arc scattering light receiving elements 12, 12b, . . . 12n, which are formed coaxially with the transmitted light detecting element 11 so as to have a wider width as they are positioned remote from the transmitted light detecting element 11. Incidentally, a reference numeral 13 denotes an isolation gap between detecting elements. The aforesaid array detector 10 receives the light scattered/diffracted at a relatively small angle of the laser beam 4A as it is diffracted or scattered by the particles in the cell 1 for various scattering angles, and then, measures their light intensity. The transmitted light detecting element 11 is used for adjusting a position optical axis and for measuring a concentration of the sample solution 2.

A reference numeral 14 denotes a multiplexor which successively captures an output (scattering light intensity signal) of the array detector 10, and successively transmits it to an A/D converter 15, and a computer 16 which functions as a processor to which an output of the A/D converter 15 is inputted. The computer 16 stores a program for processing the output of the array detector, converted into a digital signal, on the basis of a Fraunhofer diffraction theory or a Mie scattering theory, and for determining a particle size distribution of the particle group. A reference numeral 17 denotes a color display for displaying the processed results or the like.

In the aforesaid particle size distribution measuring apparatus, where the sample solution 2 is supplied to the cell 1, and the laser beam 4 from the laser beam source is irradiated to the sample cell 1, the laser beam 4 is diffracted or scattered by the particles in the cell 1. A diffracted or scattered laser beam 4A is incident upon the array detector 10 by means of the collective lens 9, and then, each output from the scattering light receiving elements 12a, 12b . . . 12n constituting the array detector 10, is amplified by means of a pre-amplifier (not shown), and thereafter, is inputted to the multiplexor 14.

In the multiplexor 14, a light intensity data for each scattering angle obtained by the array detector 10, that is, an analog electric signal is successively captured in a predetermined order. The analog electric signal captured by the multiplexor 14 is made into a serial signal, and then, is successively converted into a digital signal, and further, is inputted to the computer 16. The computer 16 processes the light intensity data for each scattering angle obtained by the array detector 10 on the basis of a Fraunhofer diffraction theory or a Mie scattering theory, and thus, determines a particle size distribution of the particle in the sample solution 2. Then, the result is displayed on the color display 17, or is stored in a memory device (not shown).

The aforesaid array detector 10 is manufactured by cutting a wafer into a predetermined shape. In the conventional case, an open (sector) angle of each element 12a to 12n constituting the scattering light detecting element group 12 has been set to a fixed angle, for example, an angle of 90°. For this reason, the array detector 10 has the following problems. More specifically, in the array detector 10, there is a need to mutually make equal the scattering light detecting characteristics of the scattering light detecting elements 12a to 12n. For this reason, as shown in FIG. 5, the array detector 10 is formed in a manner that a dimension of the respective scattering light detecting elements 12a to 12n is gradually increased in its radius direction and circumferential direction from the transmitted light detecting element 11, and also, an area thereof is increased in an exponential function. In this case, if each open (sector) angle of the scattering light detecting elements 12a to 12n is held constant, as a radius distance from the transmitted light detecting element 11 gradually becomes larger, an area of each effective light collection portion (portion shown by a symbol "a" in FIG. 5) of the scattering light detecting elements 12a to 12n is increased. For this reason, the array detector 10 is required to be of a relatively large size, and also, any equipment for holding the array detector 10 becomes large, as a result, the particle size distribution measuring apparatus will be of a large size.

Moreover, the number of the array detectors 10 capable of being manufactured from a single wafer 18 is four (4) as shown in FIG. 5, in the case where the detector element sector angle is 90°. Therefore, the number of array detectors 10 capable of being manufactured from a single wafer is limited as number; for this reason, there is an increase in cost, and as a result, the particle size distribution measuring apparatus becomes expensive.

Examples of conventional array detectors can be seen in U.S. Pat. No. 5,164,787 and U.S. Pat. No. 5,185,641.

The prior art is still seeking improved and cost efficient array detectors.

SUMMARY OF THE INVENTION

The present invention has been made taking the aforesaid problems of the prior art into consideration. It is, therefore, a first object of the present invention to provide a small and compact particle size distribution measuring apparatus which includes a compact array detector section on an improved configuration.

A second object of the present invention is to provide a compact array detector to be used in a particle size distribution measuring apparatus, which can reduce an occupancy area in the measuring apparatus.

A third object of the present invention is to provide a manufacturing method of making an array detector, which can optimize the number of array detectors from a single wafer.

To achieve the above first object, the invention defined in a first aspect provides a particle size distribution measuring apparatus which includes an array detector having a plurality of scattering light detecting elements for detecting an intensity of scattering light generated when a laser beam is irradiated from a laser beam source to a dispersed particle group for each scattering angle, and measures a particle size distribution of the particle group on the basis of a scattering light intensity signal from each scattering light detecting element.

The array detector being formed so that a plurality of scattering light detecting elements are located on one detection plane in one radius direction with the use of an optical path as the center, and so that the maximum sector angle is obtained within a width previously set, and individual detector elements can have different sector angles.

The array detector include a first plurality of detector elements having a constant sector angle, e.g. 90° and a second plurality of detector elements having sector angles that are reduced in size With detector areas that are increased in size as they are further positioned from an optical axis.

To achieve the above second object, the invention provides an array detector which has a plurality of scattering light detecting elements for detecting an intensity of scattering light having a small scattering angle for diffraction/scattering light generated when a laser beam is irradiated from a laser beam source to a dispersed particle group for each scattering angle. The plurality of scattering light detecting elements being located on one detection plane in one radius direction with the use of an optical axis of the irradiating light source as the center, and being formed so that a maximum sector angle is obtained within a width previously set, and their sector angles are not set so as to become constant.

To achieve the above third object, the invention provides a manufacturing method for an array detector which is formed so that a plurality of scattering light detecting elements are cut out of a single wafer, the plurality of scattering light detecting elements being located on one detection plane in one radius direction with the use of an optical axis as the center, and being deposited on the wafer so that the maximum sector angle is obtained within a maximum width previously set, and their sector angle is not set so as to become constant.

According to the present invention, the array detector is manufactured so that the width $W_n$ of the scattering light detecting element situated on the farthest position from the center of the transmitted light detecting element does not exceed the maximum width W previously set. Thus, in the case of the same number of elements, an occupancy area of the array detector is made small on a single wafer, and therefore, a compact and cheap array detector can be obtained.

BRIEF DESCRIPTION OF THE DRAWINGS

The objects and features of the present invention, which are believed to be novel, are set forth with particularity in the appended claims. The present invention, both as to organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved particle measuring apparatus with a detector array and method of manufacturing the same.

Figure 1:
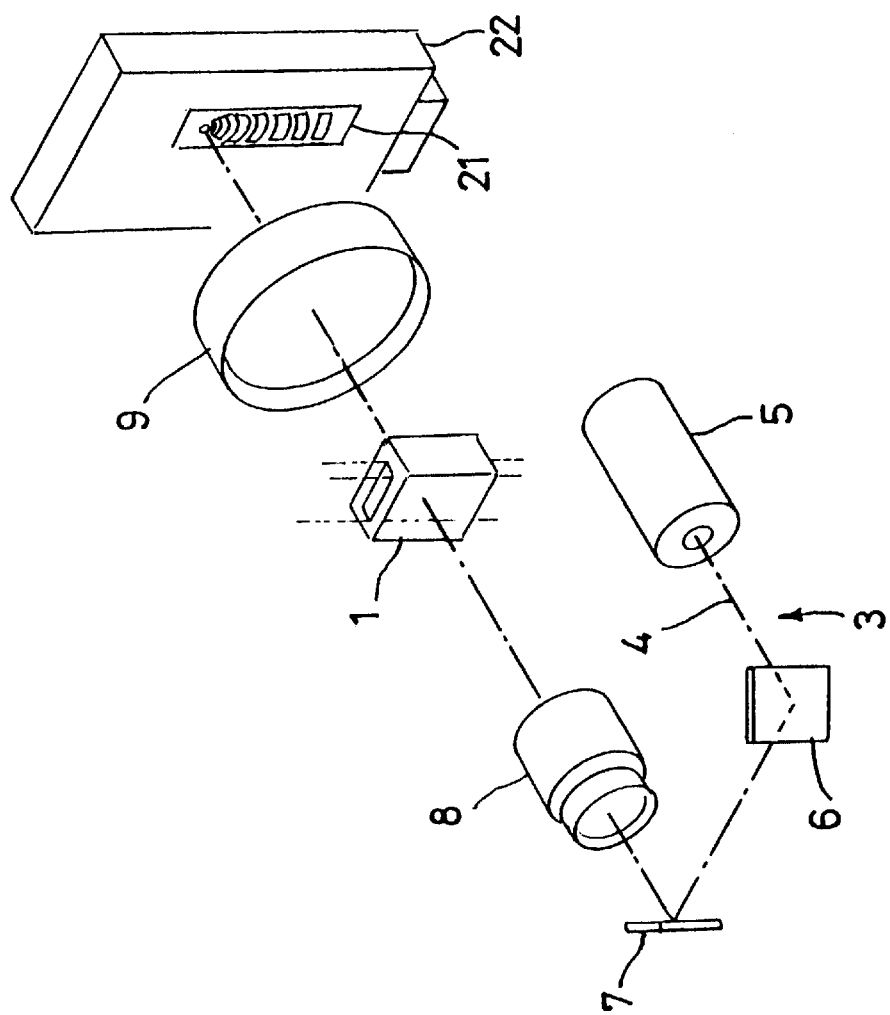
FIG. 1 is a view schematically showing a construction of principal parts of a particle size distribution measuring apparatus of the present invention.
Figure 2:
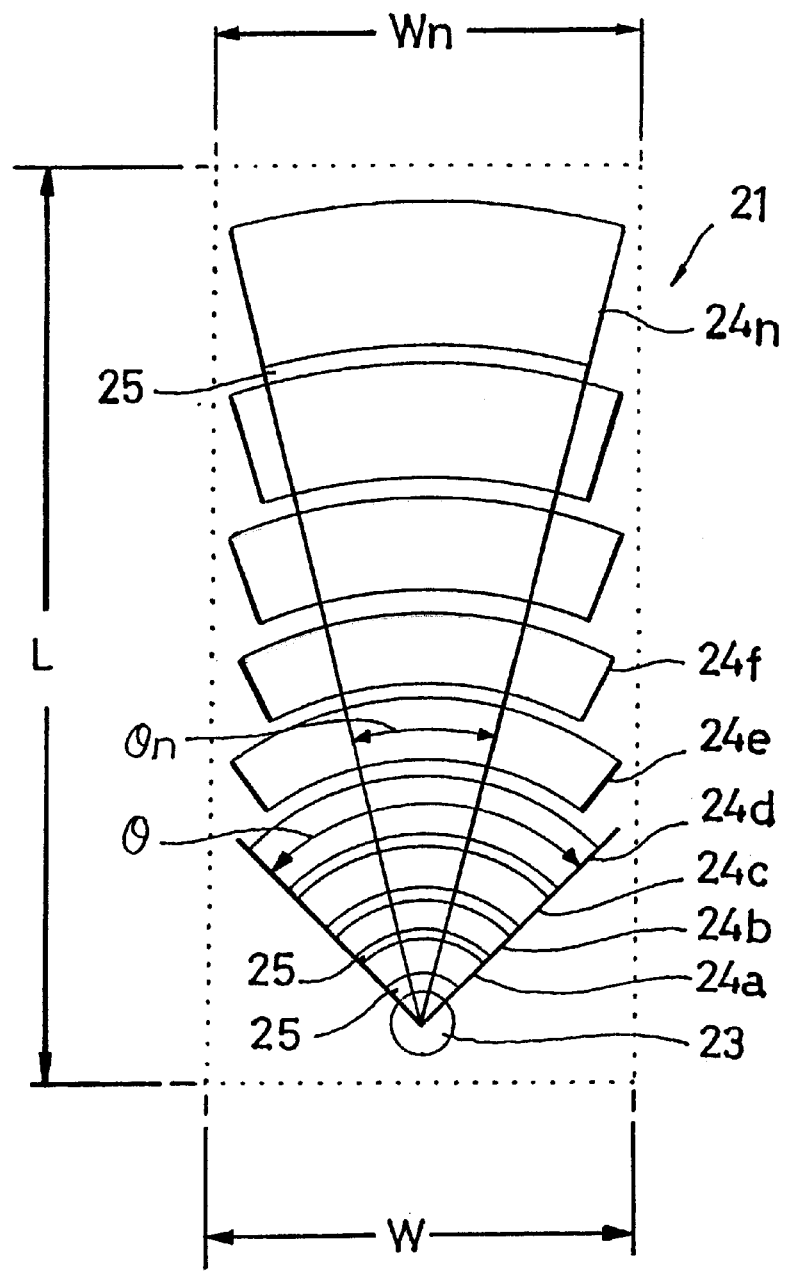
FIG. 2 is a top plan view schematically showing a construction of an array detector of the present invention.
Figure 3:
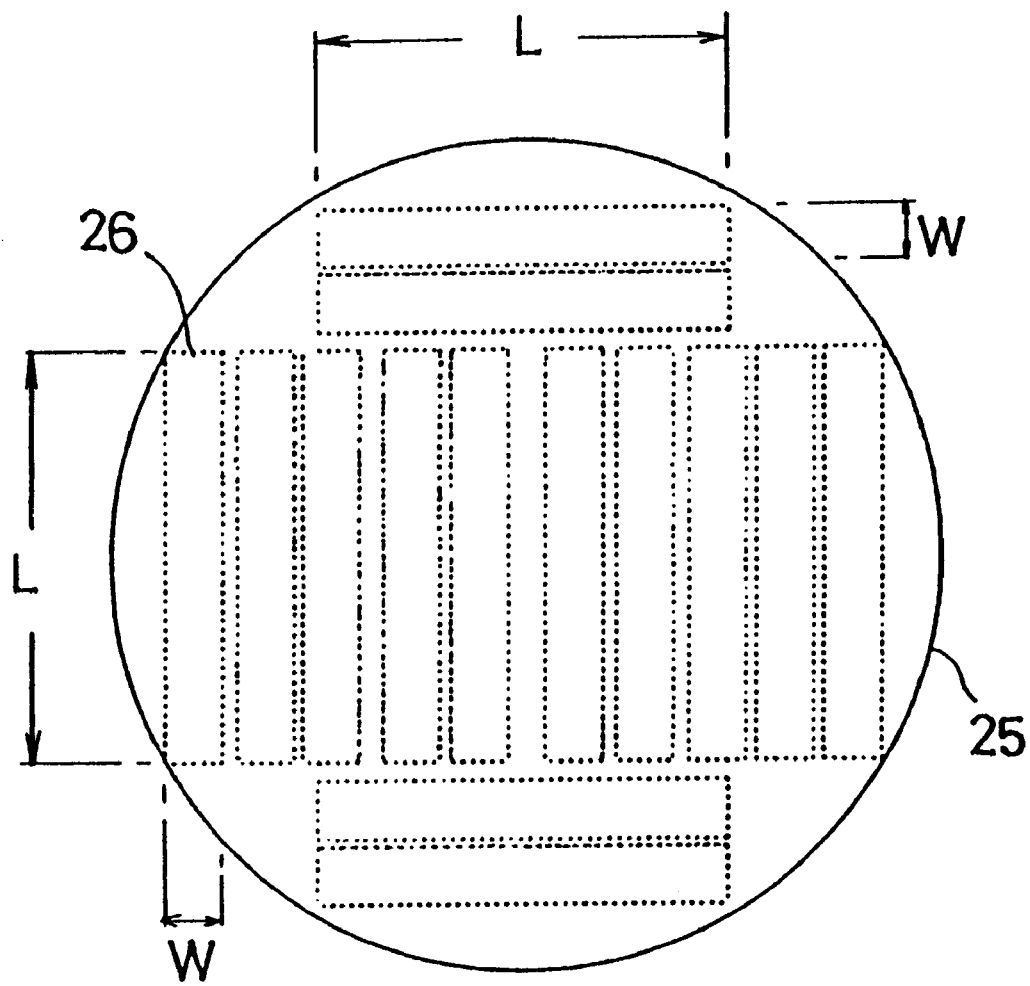
FIG. 3 is an explanatory view for manufacturing array detectors from a single wafer.

FIG. 1 to FIG. 3 show one embodiment of the present invention. FIG. 1 is a view schematically showing a construction of the principal parts of a particle size distribution measuring apparatus of the present invention. Reference can be made to "Light Scattering By Small Particles" by H. C. van de Halst, Dover Publications 1981 as background reference for scattering theory.

Figure 4:
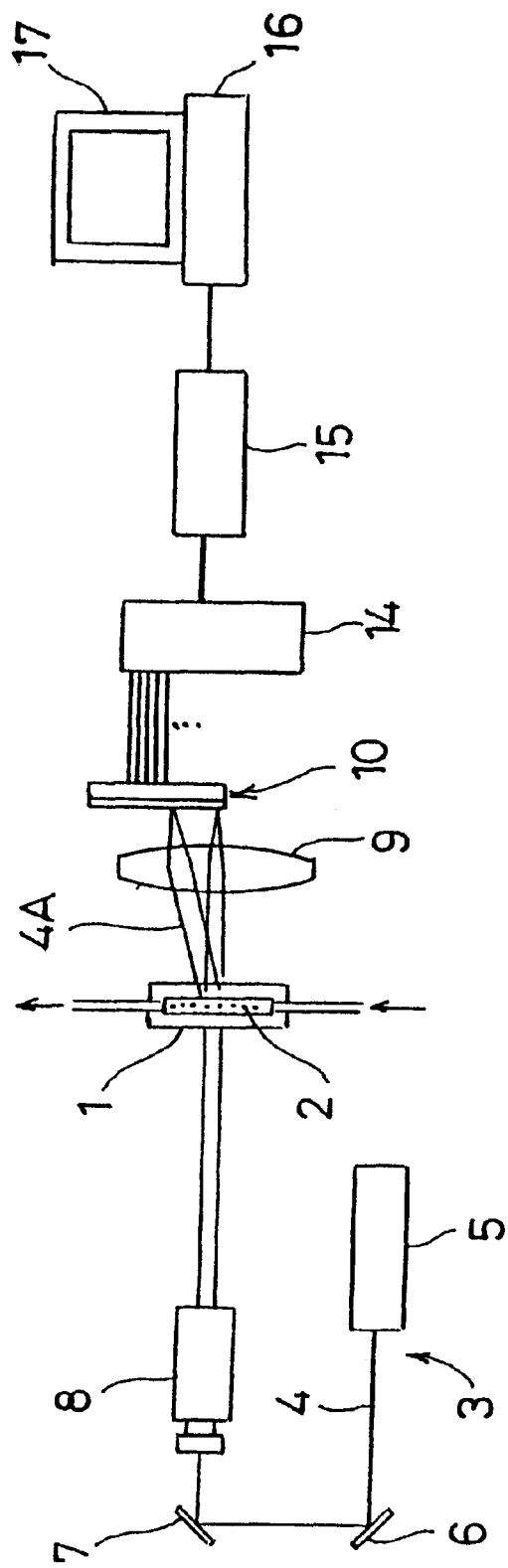
FIG. 4 is a view schematically showing a construction of a conventional particle size distribution measuring apparatus.
Figure 5:
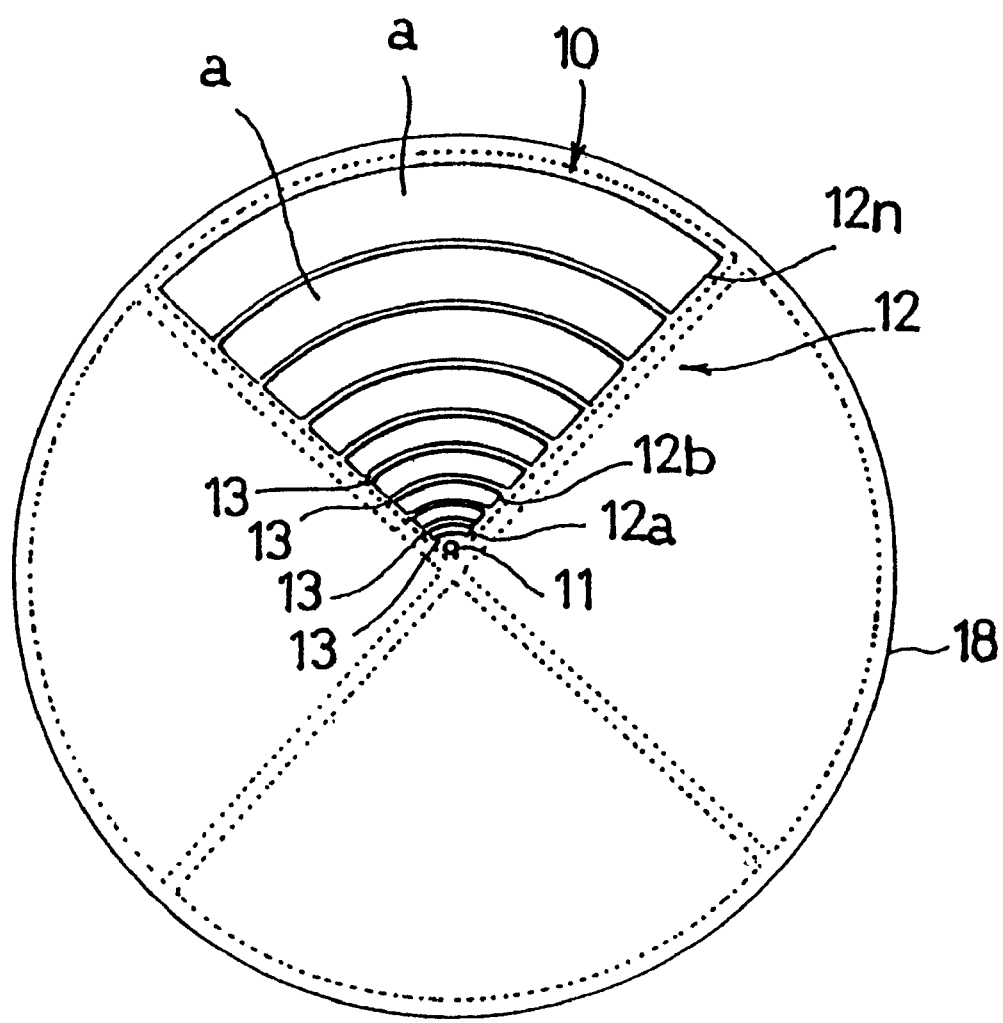
FIG. 5 is a view to illustrates a problem in a conventional array detector.

In FIG. 1, like reference numerals are used to designate the same components as shown in FIG. 4, and therefore, their details are omitted. An array detector 21 is attached to a detector retaining member 22 and is vertically located thereon. The array detector 21 is different from the conventional array 10 shown in FIG. 4 and FIG. 5 in the following points. More specifically, a plurality of scattering, light detecting elements are located on one detection plane of a substrate in one radius direction around an optical axis, and these scattering light detecting elements are formed so that their maximum sector angles are obtained within a preset width, and all of the angles are not set to be constant or equal. The manufacturing method of the above array detector will be described below with reference to FIG. 2 and FIG. 3.

FIG. 2 is a top plan view schematically showing a construction of an example of an array detector 21 of the present invention. In FIG. 2, a reference numeral 23 denotes a transmitted light detecting element for adjusting an alignment of the detector array with an optical axis of an irradiating light source and for measuring a sample fluid concentration. The transmitted light detecting element 23 when aligned corresponds to a position on an optical axis of the particle measuring apparatus. Reference numerals 24a to 24n denote a plurality of circular-arc scattering light detecting elements which are formed concentrically with the transmitted light detecting element 23 so as to have a radius wider width when located further from the transmitted light detecting element 23. These scattering light detecting elements 24a to 24n are formed so that their dimensional sizes are gradually increased in their radius direction, and their sector area is increased as they extend outward far from the transmitted light detecting element 23. A reference numeral 25 denotes an isolation gap formed between the transmitted light detecting element 23 and an upper arc boundary and lower arc boundary of each of the scattering light detecting elements 24a to 24n. The construction described thus far is almost the same as the conventional array detector 10.

In the array detector 21 of the present invention, each sector angle of the scattering light detecting elements 24a to 24n is not set so as to become constant (e.g., angle of 90°) like the conventional case, but is set so that the maximum sector angle can be obtained in a preset width. More specifically, as seen from FIG. 2, in a first group of scattering light detecting elements, that is, reference numerals 24a to 24d in illustration, which are near the transmitted light detecting element 23 situated on the center of the sector, their sector angle Θ is mutually equal, and is set so as to become an angle of 90°, for example.

In a second group of scattering light detecting elements 24e to 24n which are situated outside the scattering light detecting element 24d, a width shown by a symbol W in FIG. 2 is previously set. Thus, their sector angle of the scattering light detecting elements 24e to 24n is set so as to gradually become smaller. For example, there is the case where a sector angle Θn of the farthest scattering light detecting element 24a becomes less than 30°. Additionally, a medium circumferential distance of the sectors of the second group approximate an outermost edge distance, e.g. corner points, between the respective corners of the most radial sector, 24d, of the first group of detector elements.

Namely, in the above array detector 21, the first group of scattering light detecting elements 24a to 24d satisfy a condition such that their dimension is gradually increased in their radius direction and also in a circumferential direction, and their area is increased. The same sector angle is maintained. The scattering light detecting elements 24e to 24n are formed so that a maximum sector angle can be obtained within a preset width dimension W. In the array detector 21 constructed in the manner as described above, the whole dimension is set within a range of a rectangular shape having a width W and a length L; therefore, the occupancy area becomes considerably small as compared with the conventional array detector 10.

In the case of manufacturing the above array detector 21, for example, as shown in FIG. 3, a wafer 25 having a diameter 8 inches is sized to a rectangular portion 26 having the maximum width W and length L. And then, a portion equivalent to the transmitted light detecting element 23 is set at the center on one side in the width direction of the rectangular portion 26, and thereafter, the plurality of scattering light detecting elements 24a to 24n are formed as described above with the use of the set transmitted light detecting element 23 as the center. According to the manufacturing method of the array detector 21 of the present invention, an occupancy area of the array detector 21 becomes small. Therefore, it is possible to manufacture the array detector 21 having the same performance as the conventional case from a single wafer, and to increase the number of array detectors by three to four times as much as the conventional case for the same size wafer, and thereby, a significant cost reduction can be achieved.

The array detector 21 formed as described above is attached to the detector retaining member 22 so that the transmitted light detecting element 23 coincides with an optical axis of the collective lens 9.

As described above, according to the present invention, as shown in FIG. 2, the array detector 21 is manufactured so that the width $W_n$ of the scattering light detecting element situated on the farthest position from the center of the transmitted light detecting element 23 does not exceed the maximum width W previously set. Thus, it is possible to solve the problem that the effective area of the scattering light detecting elements 24a to 24n is increased as a radius from the transmitted light detecting element 23 becomes large; therefore, a compact array detector can be manufactured. In the case of the same number of elements, an occupancy area of the array detector is made small in the single wafer 25, and therefore, it is possible to manufacture the array detector 21 in quantities of several times the conventional case from a single wafer 25, and to reduce manufacture cost. Moreover, the detector retaining member 22 for retaining the compact array detector 21 is made into a small size as compared with the conventional case. Therefore, this serves to also make small the particle size distribution measuring apparatus, and to achieve a cost reduction.

The provision of an increased number of detector elements on a single elongated rectangular substrate lowers the cost and improves the alignment in the measuring apparatus.

The present invention is not specially limited to the above embodiment, and various modifications may be carried out. For example, in the particle size distribution measuring apparatus, in addition to the array detector 21, the following optical detecting group for wide-angle scattering light may be located in the vicinity of the cell 1, more specifically, the optical detecting group for wide-angle scattering light detects each light scattered/diffracted at a relatively large angle of the laser beam 4A diffracted or scattered by the particles in the cell 1 for each scattering angle, and thus, measures a particle size distribution of a further micro particle.

The laser beam 4 irradiated to the cell 1 does not always need to be a parallel beam. A semiconductor laser may be used as the laser beam source 5, and the collective lens may be interposed between the semiconductor laser and the cell 1 so that a converged laser beam can be irradiated to the cell 1.

Moreover, the cell 1 does not need to be a circulating type, and the target for measurement may be a powder or particle dispersed in a gas or solid, in addition to particles in a liquid.

According to the present invention, the width of the scattering light detecting element in the array detector is limited to a predetermined width; therefore, a compact array detector can be manufactured. Further, it is possible to manufacture many array detectors from a single wafer, and to reduce a manufacture cost of the array detector. Furthermore, the device for retaining the compact array detector is made into a small size, and therefore, it is possible to make small the particle size distribution measuring apparatus, and to achieve a cost reduction.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An array detector for a particle size distribution measuring apparatus, comprising:

a substrate having an elongated rectangular shape; and a plurality of light detecting elements located on the substrate, each light detecting element having a radial width between an upper arc boundary and a lower arc boundary and a pair of radial sides defining a sector angle from a predetermined position to reside on an optical axis whereby, each light detecting element forms a sector that is spaced from an adjacent sector including a first group of detector elements having a plurality of sectors with a common sector angle and at least one other detector element with a smaller sector angle wherein the first group of detector elements are positioned adjacent the predetermined position and the detector element with the smaller section angle is positioned further away from the predetermined position than the first group of detector elements, and wherein each and every upper arc boundary can be bisected by a single radial line extending from the predetermined position on the optical axis.

2. The array detector of claim 1 wherein the detector element with the smaller sector angle is part of a second group of detector elements and the second group of detector elements includes a plurality of sectors with different sector angles.

3. The array detector of claim 2 wherein a median circumferential distance of each sector of the second group of detector elements approximates an outermost edge distance between the edges of the most radial sector of the first group of detector elements.

4. An improved particle size distribution measuring apparatus for determining the size and distribution of particles in a sample, comprising:

an array detector having a substrate;

a plurality of light detecting elements located on the substrate, each light detecting element having a radial width between an upper arc boundary and a lower arc boundary and a pair of radial sides defining a sector angle from a predetermined position to reside on an optical axis whereby, each light detecting element forms a sector that is spaced from an adjacent sector including a first group of detector elements having a plurality of sectors with a common sector angle and at least one other detector element with a smaller sector angle inscribed within the common sector angle; and means for measuring a particle size distribution from an output of the plurality of light detecting elements, wherein the detector element with the smaller sector angle inscribed within the common sector angle is positioned further away from the predetermined position than the first group of detector elements.

5. The improved particle size distribution measuring apparatus of claim 4, wherein the detector element with the smaller sector angle inscribed within the common sector angle is part of a group of detector elements and the second group of detector elements includes a plurality of sectors with different sector angles inscribed within the common sector angle.

* * * * *